United States Patent
Beer et al.

[11] Patent Number: 5,739,316
[45] Date of Patent: Apr. 14, 1998

[54] CROSS-LINKED CELLULOSE HYDRATE MEMBRANES

[75] Inventors: Hans Beer, Bösinghausen; Wolfgang Demmer, Göttingen; Hans-Heinrich Hörl, Bovenden; Dieter Melzner; Dietmar Nussbaumer, both of Göttingen; Hans-Weddo Schmidt, Hardegsen; Eberhard Wünn, Roringen, all of Germany

[73] Assignee: Sartorius AG, Gottingen, Germany

[21] Appl. No.: 645,650

[22] Filed: May 16, 1996

[30] Foreign Application Priority Data

May 26, 1995 [WO] WIPO .............. PCT/EP95/02009

[51] Int. Cl.[6] .............. C07H 5/04; C08B 37/00; C08B 11/00; C12Q 1/34
[52] U.S. Cl. .............. 536/56; 536/55.3; 536/106; 536/84; 536/57; 536/59; 549/512; 435/254.6; 435/18; 548/317.1
[58] Field of Search .............. 536/55.3, 56, 106, 536/84, 57, 59; 549/512; 435/254.6, 18; 548/317.1

[56] References Cited

U.S. PATENT DOCUMENTS 4,175,183  11/1979  Ayers .............. 536/57
4,459,392  7/1984  Arai et al. .............. 525/438

FOREIGN PATENT DOCUMENTS 4418831  1/1996  Germany.

*Primary Examiner*—Louise Leary
*Attorney, Agent, or Firm*—Chernoff, Vilhauer, McClung & Stenzel, LLP

[57] ABSTRACT

A process for cross-linking a cellulose hydrate membrane by use of a water-soluble diepoxide in an alkaline solution. The membrane so produced is highly resistant to attack by alkalis, acids and cellulases, and is readily regenerable by alkaline cleaning.

14 Claims, 3 Drawing Sheets

CROSS-LINKED CELLULOSE HYDRATE MEMBRANES

This invention concerns hydrophilic, porous membranes of cross-linked cellulose hydrate, a process for their production and the use of such membranes for the filtration of aqueous media.

BACKGROUND OF THE INVENTION

Porous membranes include reverse osmosis membranes and ultra- and microfiltration membranes, in which the filtration process is based on a hydrostatic pressure differential, which is used as the driving force. Ultrafiltration membranes are characterized by pore sizes which enable them to retain macromolecules having a molecular weight ranging between 500 and 1,000,000 daltons. Microfiltration membranes exhibit permselective pores ranging in diameter between 0.01 and 10 μm. Reverse osmosis membranes are characterized by having pore sizes which retain molecules and ions having a molecular weight of ≦500 daltons. The present invention is not concerned with reverse osmosis membranes.

Cellulose hydrate membranes are well known in the membrane filtration art and present a unique combination of advantageous characteristics, including hydrophilicity, which permits wettability without the use of surfactants. Such membranes also exhibit minimal protein adsorption, high resistance to heat, resistance to most organic solvents, and high flexibility.

The use of cellulose hydrate membranes, principally in the filtration of aqueous systems, remains extensive, notwithstanding a wide range of substantial disadvantages in technical applications. Such disadvantages include susceptibility to attack by strong acids and bases, and by cellulase enzymes and the liberation of "pseudopyrogens". The attack of alkalies on cellulose hydrate membranes is characterized initially by shrinkage and swelling, which ultimately leads to decomposition of the membrane. High temperatures favor chemical disintegration and shrinkage while low temperatures, especially in connection with substantial concentrations of alkali, promote swelling and bursting. The alkali sensitivity of cellulose hydrate membranes is a marked disadvantage when, for example, strongly alkaline cleaning media are required to clean the membrane to restore its filtration capacity.

Acid attack of cellulose hydrate membranes leads to a chemical decomposition of the cellulosic groups all the way down to glucose, and is encountered in industrial applications with the use of strongly acidic cleaning media. At high temperatures even weak organic acids can lead to the destruction of cellulose hydrate membranes. When, for instance, a steam sterilization is carried out without sufficient rinsing following the filtration of wine, which contains weak organic acids, the cellulose hydrate membrane can suffer a loss in tensile strength to the point of total disintegration of the membrane.

Cellulases are encountered in the brewing industry, and also develop spontaneously from molds that grow on cellulose hydrate membranes during prolonged storage in a non-sterile environment. Cellulases attack cellulose hydrate membranes by decomposing the cellulosic polysaccharids therein into smaller chemical fragments such as glucose.

When cellulose hydrate membranes decompose, some of the byproducts of the decomposition lead to the formation of so-called "pseudopyrogens" or fever-producing substances. The emission of such pseudo-pyrogens can lead to false positive test results with many Limulus test kits on the market. This militates against the use of cellulose hydrate membranes in the filtration of pharmaceutical products. In this vein, it is particularly disturbing that pseudopyrogens can be formed anew, even after heat sterilization and rinsing.

From the experience of the textile industry, it has long been known that better characteristics may be imparted to cellulosic fibers by cross-linking. The cross-linking of cellulose (i.e., native cellulose, cellulose hydrate, and regenerated cellulose) through the hydroxyl groups of the glucose components was a subject intensively researched, particularly on cotton and regenerated cellulose fibers. See Kirk-Othmer's *Encyclopedia of Chemical Technology*, Vol. 22, pp 770–790 (3rd Ed. 1983). However to date, attempts to apply this technology to membrane filter production have not led to satisfactory results.

A process for cross-linking cellulose hydrate membranes is disclosed in EP 0 145 127, the process comprising contacting cellulose hydrate membranes with a solution of a cross-linking agent. However, the cross-linked membrane products exhibited considerable degradation in their hydrophilic properties as compared to the original membrane. Cross-linking agents disclosed were bis-(2-hydroxyethyl) sulfonate, dimethyldichlorosilane, epichlorhydrin, formaldehyde, dimethylolurea, dimethylol ethylene urea and diisocyanate. Because of the substantial degradation of hydrophilic properties of such cross-linked cellulose hydrate membranes, their range of application in aqueous media separations is severely restricted. Moreover, with increased cross-linking, the flux of such membranes dramatically decreases by about 80% from the flux of a non-cross-linked cellulose hydrate membranes. Cross-linking with the epoxide epichlorhydrin, because of its low water-solubility, requires the use of organic solvents, which also makes the process technically difficult and expensive.

Accordingly, the objects of the invention are to cross-link cellulose hydrate membranes in an efficient process that does not modify their hydrophilic properties, high flux and minimal protein adsorption, and so as to impart to the membranes an increased resistance to acids, bases and cellulases so as to minimize degradation and eliminate the accompanying production of pseudopyrogens.

SUMMARY OF THE INVENTION

The foregoing objects are achieved by a process for cross-linking cellulose hydrate membranes, the essential step of which comprises contacting the membrane with a water-soluble diepoxide. Such membranes can be used for all ultra- and microfiltration applications, where both low protein adsorption and high chemical resistance of the membrane are required. In a preferred embodiment, the water-soluble diepoxide has a water-solubility of ≧0.2M and is miscible with water. Most preferably the diepoxide is 5-ethyl-1,3-diglycidyl-5-methylhydantoin.

By virtue of their high capacity and long life, and resistance to alkaline liquors, acids and cellulases, the cross-linked membranes of the present invention are markedly superior to those currently commercially available, and find application in the food and beverage industries, in environmental protection, in the chemical and pharmaceutical industries, and in medical technologies. The process for the manufacture of the membranes is low cost and environmentally friendly as well.

DETAILED DESCRIPTION OF THE PREFERRED EMBODIMENTS

Figure 1:
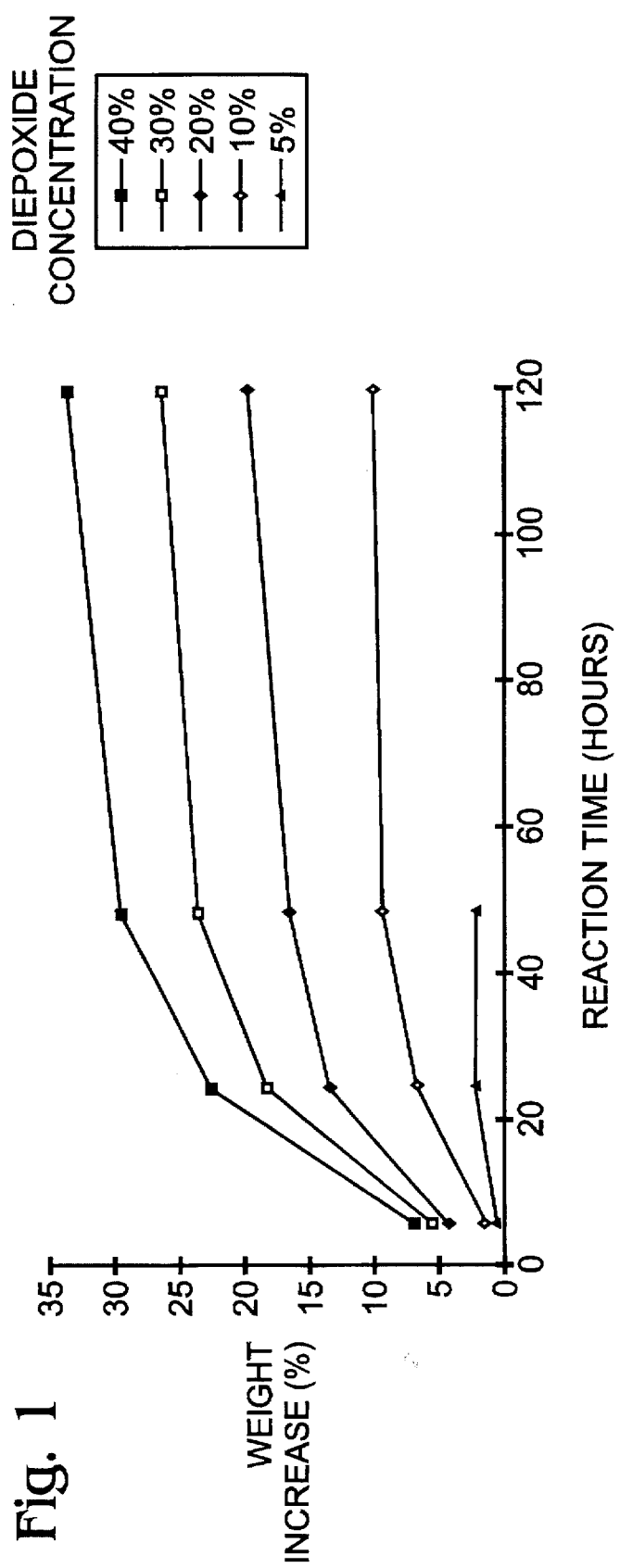
FIG. 1 is a graph relating the weight increase to the reaction time of cellulose hydrate microfiltration membranes after cross-linking in accordance with the invention.

The average degree of substitution of the anhydroglucose units of cellulose by reaction with the diepoxide is used as a measure of the degree of cross-linking (DX). This measure assumes that each of the two epoxide groups of the diepoxide reacts with the cellulose, from which wt % increase can be determined. The theoretical maximum value of DX is set at 3, based on the three hydroxyl groups of the anhydroglucose. From the known molecular weight of anhydroglucose of 162 daltons, the relationship between the degree of cross-linking (DX), molecular weight (M) of the diepoxide in daltons and the wt % increase (dM) relative to the initial weight is given by the following equation:

$$DX = 3.24 \times \frac{dM}{M}$$

In the case of supported membranes, the values given for weight increases and decreases refer strictly to the cellulose component of the composite membrane. Moreover, tests that report an increase in surface area of a membrane by swelling herein refer only to unsupported membranes.

A convenient test for judging the alkali resistance of cellulose hydrate membranes is: after a one-hour treatment with a 10% sodium hydroxide solution at 7° C., the weight loss, the degree of swelling, the increase in surface area and the reduction of water flux are determined. Non-cross-linked cellulose hydrate membranes subjected to such treatment are rendered practically completely soluble. It has been found that the resistance to alkaline liquors, acids and cellulases increases with the degree of cross-linking; a degree of cross-linking of 0.05–0.4 in cellulose hydrate membranes produced in accordance with the present invention shows a weight loss of less than 10% and a surface swelling of far less than 50% when subjected to the aforementioned test. Further, the reduction in water flux is also well within acceptable limits. Beyond this, it has been determined that the membranes exhibit stability against degradation by alkaline cleaning agents used on a daily basis.

With respect to resistance to attack by acid, a 15-minute treatment with boiling, 1N sulfuric acid will totally disintegrate non-cross-linked cellulose hydrate membranes, while the membranes cross-linked in accordance with the present invention suffer a weight loss of less than 5%. This criterion is not valid for a test for the acid resistance of cellulose hydrate membranes, because acid-treated cross-linked membranes are rarely seriously damaged in their tensile strength notwithstanding a small weight loss. In any event, it has been shown that a cross-linked membrane's high resistance to alkali also means good resistance to acid attack.

Since it is known that cellulose hydrate membranes having a cross-linking degree of 0.05 are resistant to attack by enzymes, membranes prepared in accordance with the invention are, in every case, resistant to cellulase.

A particularly preferred range for the degree of cross-linking is from 0.12 to 0.25. Upon subjecting cellulose hydrate membranes having this degree of cross-linking to the alkali resistance test noted above, the membranes exhibited weight loss of less than 5%, swelling of less than 15% and a reduction in water flux of less than 20%. In addition, virtually no pseudopyrogen emission was observed.

In the case of cross-linkage degrees greater than 0.4, normally the flexibility of the cross-linked membranes markedly decreases, so that their workability becomes difficult, and hence expensive. This loss of flexibility exhibits itself in a tendency to fracture upon bending when dry, and in extreme cases, even when wet. Within the range of weight percent increase shown in FIG. 1, microfiltration membranes exhibit an increase of up to about 20% in water flux. On the other hand, in the case of ultrafiltration membranes, a 50% decrease in water flux is observed, which, however, is also accompanied by a corresponding increase in protein rejection. Thus, for the production of a cross-linked cellulose hydrate ultrafiltration membrane having a predetermined separation capacity, one must begin with a correspondingly larger-pore non-cross-linked membrane. With membranes cross-linked according to the present state of the art, if one attempts to prevent the loss of hydrophilicity by limiting the degree of cross-linking to a minimal amount, then the membrane will show signs of not being resistant to strong bases and to acids.

Surprisingly, it has been found that by the use of a water-soluble diepoxide as a cross-linking agent, even high degrees of cross-linking, such as greater than 0.4, have virtually no impact whatsoever upon the hydrophilic properties of the membrane. For example, the absorption of drops of water placed on membranes of non-cross-linked cellulose hydrate membranes and membranes prepared in accordance with the invention was compared; no difference in absorption rates was observed. Similarly, no difference in the resistance to the adsorption of proteins was observed between membranes prepared in accordance with the present invention and non-cross-linked cellulose hydrate membranes. Although not wishing to be bound by any theory, it is believed that such a retention of hydrophilicity and low protein adsorption are due to the hydrophilic nature of the cross-linking agent itself, a property which results in its water-solubility.

Cross-linking of microfiltration membranes can be carried out either in a wet or dry procedure. In the case of ultrafiltratioh membranes, fabrication is carried out only according to a wet process; this process is characterized by the application of an aqueous solution of the diepoxide cross-linking agent in a concentration of 0.2 to 2.0M, preferably 0.3 to 0.8M, together with 0.05 to 0.3, preferably 0.1 to 0.2 equivalent/liter of a strong alkaline liquor as a catalyst. After the cross-linking, the membrane is rinsed with lightly acidic water, for instance, 5 wt % acetic acid. In order to retain their full flux, ultrafiltration membranes are impregnated with an aqueous solution of glycerine prior to drying. Microfiltration membranes may also be impregnated by glycerine, but in this case it is not necessary for the retention of the membrane flux.

In the case of the wet process, the cross-linking solution advantageously also contains an inorganic salt such as sodium sulfate up to its maximum concentration, which leads to turbidity of the solution due to the salting out of the diepoxide. The reaction temperature is preferably from about 0° to about 50° C., with room temperature being most preferred. The reaction time at room temperature is from 5 to 96, preferably from 48 to 72 hours, while the cross-linking reaction may take place in a bath of the cross-linking solution or preferably by impregnation of a continuous membrane sheet with the cross-linking solution, followed by storage of the impregnated membrane in rolls at reaction temperature. In connection with the storage of the impregnated rolls, care should be taken to avoid drying, for instance, by wrapping the membrane sheet in impermeable plastic.

Ultrafiltration membranes cannot be impregnated with the cross-linking solution in the dry state, but only while they are wet. Otherwise the membrane will be irreversibly damaged. In such cases, the impregnation of a membrane sheet is accomplished in several passes by repeated dosing of the treating solution with the diepoxide, the alkaline liquor and, if necessary, the neutral salt, until the concentration of the cross-linking solution remains constant, the concentration being best monitored by monitoring the solution's density or specific gravity.

The alkaline liquor acts as catalyst for the wet process, not only for the reaction of the diepoxide with the cellulose, but also in deactivating the effect of water on the cellulose. Relative to the amount of diepoxide used, the next factor in order of importance in maximizing yields is the concentration of alkali in the cross-linking solution or dope. Next in importance is the volume of diepoxide dope relative to the membrane surface area; an especially preferred ratio is 200–250 ml dope per square meter of membrane. The reaction time is preferably so chosen, that virtually all of the diepoxide is consumed by the end of the reaction, so as to render unnecessary subsequent waste water treatment for removal of residual epoxides. The impregnation process is therefore preferred, not only because of its simplicity, but also because of the efficiency achieved by the use of 200–250 ml/m$^2$ of diepoxide dope.

The addition of a neutral salt to the cross-linking solution enhances the reaction yield markedly in the sense that in the presence of the neutral salt, the same degree of cross-linking is attainable with a lower concentration of the cross-linking agent, as compared to cross-linking without a neutral salt. By this procedure, the commercial value of the process is increased. As to what chemical mechanism contributes to this enhanced yield, that is, whether the reaction with water is slowed in the presence of the neutral salt, or whether the reaction with cellulose is accelerated, is as yet unclear.

The water-solubility of the cross-linking agent is also an important factor in the present invention, because otherwise the cross-linking may not be effected in a homogenous, aqueous medium nor in a single step. In order to attain a degree of cross-linking of at least 0.05, a minimum concentration of 0.2M diepoxide is required. In the case of the wet process, no increase in the degree of cross-linking is attained by increased reaction times beyond 96 hours, nor by an increase of the alkali concentration because of the side reaction with water previously mentioned. The cross-linking reaction may only be carried further by the use of a fresh solution of cross-linking agent.

By comparison, using the present state of technology, if a cross-linking agent such as epichlorhydrin is used, which is only minimally water-soluble, higher degrees of cross-linking may be achieved in an aqueous medium only in a two-phase system, wherein the cross-linking agent comes from the organic phase. Such two-phase systems are, however, technically difficult to handle, and may not be used at all in an impregnation-type process to achieve uniform cross-linkage over the membrane sheet.

In the dry process, the membrane is impregnated with the cross-linking agent and with or without an intermediate drying step of 30 seconds to 10 minutes when heated at a temperature between 80° and 150° C., preferably between 100° and 120° C. Because of the short reaction time of the dry process continuous cross-linking of microfiltration membranes is possible. The form of the cellulose hydrate membranes cross-linked in accordance with the invention may be flat, hollow fibers, and tubular, all of which may be incorporated into corresponding modules. Flat sheet membranes prepared in accordance with the invention may be pleated. Membranes prepared in accordance with the invention can be supported or unsupported, and matted or woven materials may be used as the support. When a cellulose support is used, this will be cross-linked along with the cellulose hydrate membrane. When non-cellulosic materials are used as the support, the weight increase through cross-linking will not apply to the support material.

The field of applications for membranes prepared in accordance with the invention includes all ultra- and microfiltration tasks, which require not only low protein adsorption but also high chemical resistance of the membranes, and minimal emission of pseudopyrogens. This is the case, for example, in the filtration of aqueous media of biologic and biotechnical origins. Biotechnically produced aqueous media and beverages contain numerous materials which attack the membranes during or after the filtration process in chemical or mechanical ways, or deposit on the membrane surface to lead to an undesired decrease of filtering capacity. For instance, mash and other insolubles, which are to be separated by means of filtration from clear beer wort, leave a mix of hulls, soluble and insoluble proteins, fats, polyphenols, other insoluble components from raw materials, water and soluble extracts of starch. These substances attack membranes or tend to blind the membrane filter by adsorption. Such blockage normally leads to a very rapid drop-off in filtration capacity.

In beer brewing, the filter membranes employed must remove the materials causing turbidity, the yeasts, and such microorganisms as are detrimental to beer, but at the same time must not adversely impact the aroma, taste and neutrality to foreign materials. This could easily happen with a blinded or partially blinded filter membrane.

Microorganisms and particularly enzymes, often encountered in biotechnically produced media and in beverages such as beer, cannot be allowed to attack the membrane material employed in the filtration membranes. If one uses membranes of cellulose hydrate, cellulases either from brewing or from molds that have grown on the membrane itself can totally destroy such membranes. Wine contains polyphenols and organic acids, both of which cause problems in the filtration process. If, for instance, a steam sterilization is carried out with insufficient preliminary rinsing following a wine filtration, the cellulose hydrate membrane may suffer structural damage or even disintegration as a result of attack by residual organic acids.

Cross-linked cellulose hydrate membranes with a pore size in the range of 0.01 to 10 μm, preferably 0.1 to 0.8 μm, are particularly well-adapted to the filtration of biologically and biotechnically produced liquid media and drinks, in particular for the filtration of mash, beer and wine. Such membranes are commercially valuable, as they possess high flux, low protein adsorption and a minimal tendency to become fouled in the presence of polyphenols, albumens, and fats. They are sufficiently resistant to acids, bases and cellulases, and are capable of being autoclaved, sterilized with steam, and regenerable by cleaning agents.

Cross-flow filtration of mash has shown that microfiltration membranes of cellulose hydrate prepared in accordance with the invention, even after six weeks of use, with regular regenerations with 1M sodium hydroxide, were capable of reuse at substantially the same capacity. After regeneration, flow rates of more than 95% of the original were achieved. Regenerations were carried out at that point at which a 95% drop in the flow rate from the original value was observed. The frequency of regeneration is dependent upon the shape of the module and the method of operation of the cross-flow filter equipment.

Experiments over significant periods have shown that the membranes of cellulose hydrate prepared in accordance with the present invention exhibit only a very low drop in their filtration capacity after prolonged usage. This is likely because of the minimal interaction of the substances of the medium to be filtered with the membrane material. This low drop in filtration capacity arises from the generally higher capacity of the membranes, from fewer cleaning cycles (which means fewer down times), and from a better cleaning efficiency.

Moreover, the cross-linked ultrafiltration membranes prepared in accordance with the invention are particularly suitable for the separation of aqueous/oil emulsions. The concentration of oil from aqueous/oil emulsions has commercial significance in that if the oil is disposed of by incineration, the higher concentration of oil in the retentate stream permits the production of energy. Very good results have been achieved with ultra-filtration membranes of cellulose acetate in the treatment of non-alkaline oil emulsions produced, for example, in the condensate of compressors. Such cellulose acetate membranes are seldom used in the case of strong alkaline emulsions and the same is true for the non-cross-linked cellulose hydrate membranes, because of the sensitivity of both to alkalies. Strong alkalies are often encountered in spent degreasing baths, which are nearly exclusively used now for the degreasing of metal parts.

EXAMPLE 1

Weighed, unsupported commercial grade cellulose hydrate microfiltration membranes having a nominal pore size of 0.45 μm (Type SM 116 06 from Sartorius AG) and a diameter of 50 mm were cross-linked by treatment in a beaker at room temperature for periods varying from 5 hours to 5 days, with an excess of aqueous alkaline solutions of the diepoxide 5-ethyl-1,3-diglycidyl-5-methylhydantoin (MW= 254 MW daltons). The concentration of the diepoxide was varied from 5 to 40 wt %, while the solutions were uniform in alkaline concentration at 0.1N, with reference to NaOH. Following the cross-linking treatment, the membranes were rinsed with deionized water, dried for 30 minutes at 105° C., and their percentages of weight increase were determined. The results are presented in FIG. 1.

EXAMPLE 2

A set of the same non-cross-linked membranes used as the starting material of Example 1 and the membranes cross-linked by the procedures of Example 1 were subjected to an alkali resistance test as follows: the membranes, in a water-dampened condition, were placed in a 10 wt % aqueous sodium hydroxide solution for one hour at 7° C. and subsequently laid flat on a glass plate to measure the degree of surface swelling. Since the swelling occurred generally anisotropically, the membranes took on an elliptical shape in the swelled condition. The percentage degree of surface swelling (Q) was calculated from the measured axes a and b of the ellipse and the diameter d of the original, untreated circular membrane using the following equation:

$$Q=[a(b/d^2)-1]\times 100$$

Figure 2:
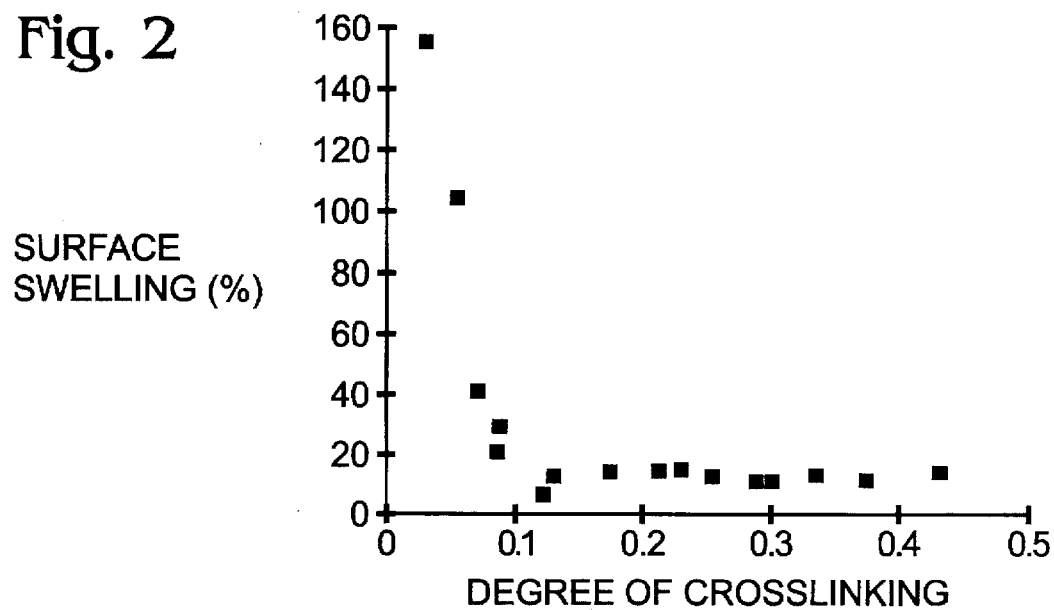
FIG. 2 is a graph relating surface swelling to the degree of cross-linking of cross-linked cellulose hydrate microfiltration membranes prepared in accordance with the invention following a one-hour treatment with 10 wt % aqueous sodium hydroxide solution.
Figure 3:
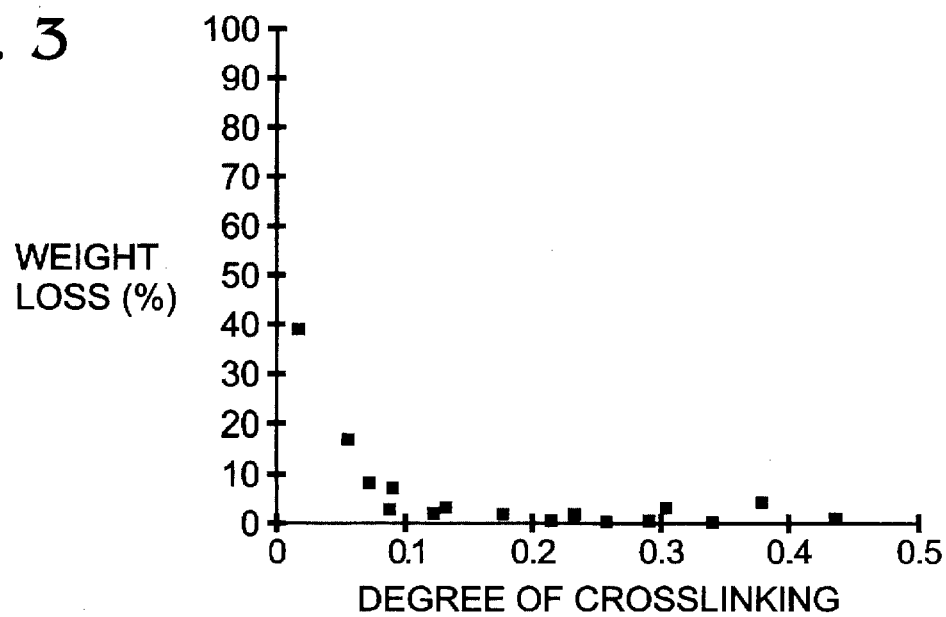
FIG. 3 is a graph relating weight loss to the degree of cross-linking of cellulose hydrate microfiltration membranes prepared in accordance with the invention following a one-hour treatment with 10 wt % aqueous sodium hydroxide solution.

The measurement results are presented in FIG. 2 wherein the abscissa shows the degree of cross-linking (DX) of the particular test. Subsequently, both non-cross-linked and cross-linked membranes were placed in a 2 wt % acetic acid solution for 5 minutes and agitated, then rinsed with deionized water, then rinsed with acetone, then dried for 5 minutes at 80° C., weighed, and the wt % loss determined in relation to the original cross-linked membrane. The results are presented in FIG. 3, wherein the ordinate shows the percentage weight loss due to the alkali liquor treatment. The percentage weight loss of the non-cross-linked membranes could not be reported, inasmuch as they were substantially dissolved.

EXAMPLE 3

In accordance with the procedures and conditions of Example 1, two sets of membranes were cross-linked with a 20 wt % 5-ethyl-1,3-diglycidyl-5-methylhydantoin 0.1N sodium hydroxide solution and with the same solution containing 2 wt % anhydrous sodium sulfate (at this concentration no turbidity of the liquor by salting out of diepoxide was observed). The results are reported in Table 1 below:

TABLE 1

| Cross-linking Time (hours) | DX Without Sodium Sulfate | DX With Sodium Sulfate |
| --- | --- | --- |
| 24 | 0.17 | 0.23 |
| 48 | 0.22 | 0.32 |

EXAMPLE 4

Cellulose hydrate ultrafiltration membranes were cross-linked in substantially the same manner as set forth in Example 3 for 72 hours in the presence of sodium sulfate and compared with the same membranes that had not been cross-linked. Both cross-linked and non-cross-linked membranes were tested at 4 bar test pressure in a static pressure cell for their hydraulic permeability (P), as well as in a agitating cell for their average cytochrome C filtration capacity ($C_{cyt}$) and average cytochrome C retention ($R_{cyt}$) (filtration of cytochrome C solution of 1 mg/ml in 0.9% aqueous sodium chloride solution conducted to a residual volume of 0.50 ml). The values found are reported in Table 2.

TABLE 2

| Type | P* | Ccyt | Rcyt |
| --- | --- | --- | --- |
| Non-cross-linked | 0.245 | 0.098 | 79.0 |
| Cross-linked | 0.185 | 0.088 | 90.6 |

*ml/cm$^2$ · min · bar

EXAMPLE 5

A cross-linked microfiltration membrane prepared according to Example 1 having a cross-linking degree of 0.05; a cross-linked ultrafiltration membrane prepared according to Example 4; corresponding non-cross-linked control samples; as well as a commercial grade supported cellulose hydrate ultrafiltration membrane (YM 30 from Amicon) were all treated for 24 hours at room temperature in a cellulase solution (30 mg/ml cellulase from *Trichoderma viride*, 1.5 U/mg, in a 0.04M sodium acetate buffer, pH 5.9 from Merck). The result: the cross-linked membranes remained intact, while the non-cross-linked samples disintegrated. Nothing was left of the Amicon membrane but the support layer.

EXAMPLE 6

A microfiltration membrane produced according to Example 1, having a cross-linking degree of 0.15; a cross-linked production grade ultrafiltration membrane; as well as a non-cross-linked microfiltration membrane control sample were all rinsed with pyrogen-free water and each was subsequently autoclaved in pyrogen-free water (1 ml/cm$^2$ membrane) to obtain a liquid extract. Commercially available Limulus tests were carried out on each membrane extract in the conventional manner according to the manufacturer's specifications. A series of dilutions of the extract, each dilution varying by a factor of 10, were prepared and the samples tested for the presence of pyrogens. The sensitivity of the tests was ascertained with *E. coli* Standard-Endotoxin and included in the quantitative evaluation. Since the test excluded the production of natural pyrogen Endotoxin, the values recorded represent pseudopyrogens released during autoclaving. These quantities in turn represent the content of Standard-Endotoxin. Table 3 reports Pseudopyrogen content in the extracts from different membranes obtained by autoclaving, representing pg/ml Standard-Endotoxin from *E. coli*.

TABLE 3

| Extract From | Non-cross-linked | Microfilter Cross-linked | Ultrafilter Cross-linked |
| --- | --- | --- | --- |
| 1st Autoclaving | 1000–10,000 | 10–100 | 10–100 |
| 2nd Autoclaving | 100–1000 | <10 | 10–100 |
| 3rd Autoclaving | 100–1000 | <10 | 10–100 |

EXAMPLE 7

One hundred grams of ground malt were suspended in water and heated with stirring in a water bath for 60 minutes at 55° C., 45 minutes at 65° C., and then 15 minutes at 75° C. The mash obtained in this manner was produced fresh for each test and used immediately in membrane filtration tests. Membranes of polyethersulfone (PES) and cross-linked cellulose hydrate (XCH) with an average pore size of 0.2 µm were compared. The XCH membrane (DX=0.1) was cross-linked by means of 5-ethyl-1,3-diglycidyl-5-methylhydantoin to a weight increase of 10%, while the PES membrane was an unsupported hydrophilic membrane (SM 15107, Sartorius AG).

Figure 4:
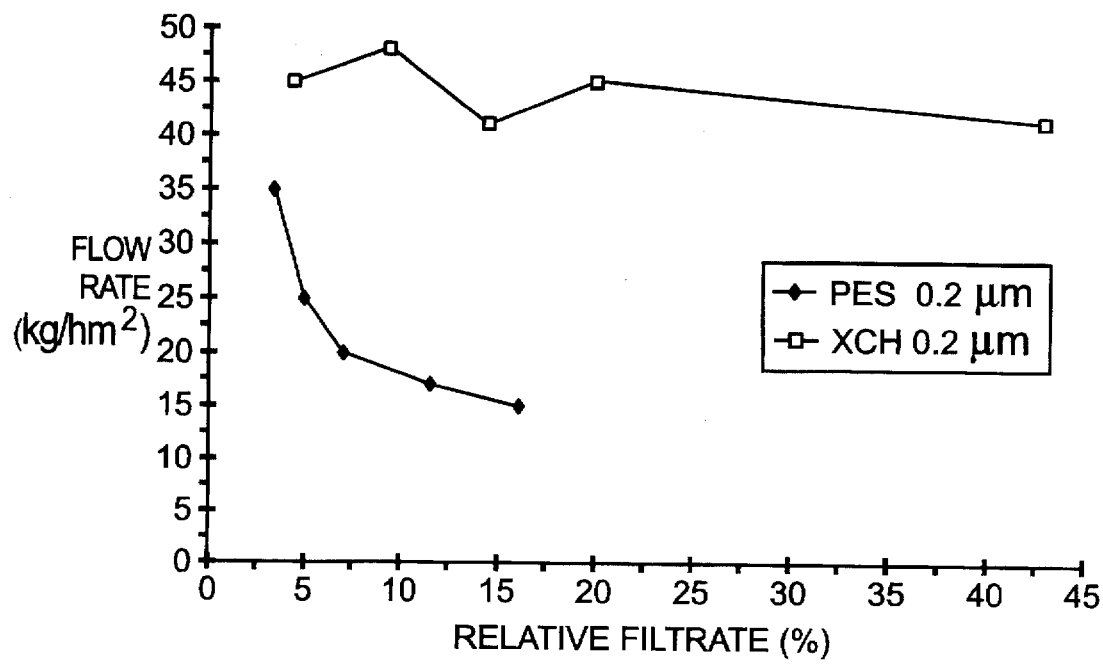
FIG. 4 is a graph of the flow rates of 0.2 µm microfiltration membranes of cross-linked cellulose hydrate and polyethersulfone, both as functions of the filtrate quantity.

Suspended mash (200 ml) was poured into a centrifugal mixing cell (Type SM 16526, Sartorius AG) equipped with a thermostat and a magnetic stirrer and capable of maintaining the mash in suspension prior to filtration, and filtered at 1000 rpm and at a pressure differential of 0.3 bar. The effective filter surface area was 12.5 cm$^2$. The filtrate was retrieved and its weight or volume periodically determined and recorded in relation to the time it took the fluid portion of the mash to pass through the filter. Filtration was continued to that point where, due to the decreased fluid content of the mash in the cell, filtration could effectively no longer take place, or until the filtrate flow rate dropped below a predetermined level. The filtration capacity of the PES membrane dropped to 46% of its original capacity after only 15% of the mash suspension was filtered. On the other hand, the XCH membrane maintained a nearly constant filtration capacity and permitted a concentration of the mash to a factor of nearly 2. The flow rates as a function of the filtrate volume are reported in Table 4 and displayed in FIG. 4.

TABLE 4

| Relative Filtrate Quantity | Flow Rate (kg/h · m$^2$) | |
| --- | --- | --- |
| (%) | PES 0.2 µm | XCH 0.2 µm |
| 3.5 | 35 | 45 |
| 4.5 | — | — |
| 5 | 25 | — |
| 7 | 20 | 48 |
| 9.5 | — | — |
| 11.5 | 17 | 41 |
| 14.5 | — | — |
| 16 | 15 | 45 |
| 20 | — | 41 |

EXAMPLE 8

Mash produced as in Example 7 was filtered in the same manner and with similar membranes to those described in Example 7. Following the filtration, the mash was removed and the membrane was treated in the stirring cell with water for 10 minutes at 70° C., then rinsed with water again and the filtration of fresh mash was carried out. The average filtration speed was observed for each filtration.

The PES membrane and the XCH membrane each had an average pore size of 0.45 µm. The XCH membrane was cross-linked in accordance with Example 1 up to a weight increase of 15%, and had a degree of cross-linking of 0.2, while the PES membrane was supported with a saponified polyvinyl acetate hydrophilic membrane (Sartorius AG).

Figure 5:
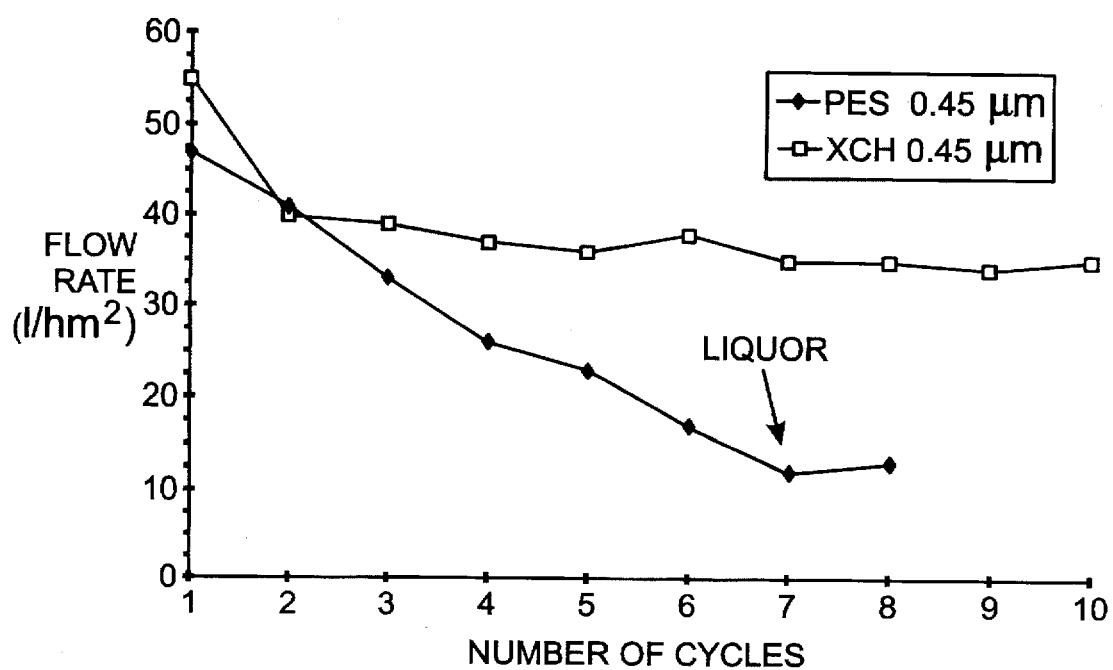
FIG. 5 is a graph of the flow rates of 0.45 µm microfiltration membranes of cross-linked cellulose hydrate and of polyethersulfone, both as a function of the number of filtrate cycles.

The filtration capacity of the PES membrane dropped off sharply with each filtration cycle and only minimally increased when cleaned with NaOH (10 min, 70° C). On the other hand, the XCH membrane showed only a minimal decline in the filtration capacity, which was completely restored after the same NaOH cleaning. The data obtained are presented in Table 5 and displayed in FIG. 5.

TABLE 5

| | Flow Rate (l/h · m$^2$) | |
| --- | --- | --- |
| No. Cycles | XCH 0.45 µm | PES 0.45 µm |
| 1 | 55 | 47 |
| 2 | 40 | 41 |
| 3 | 39 | 33 |
| 4 | 37 | 26 |
| 5 | 36 | 23 |
| 6 | 38 | 17 |
| 7 | 35 | 12 |
| 8 | 35 | 13 |
| 9 | 34 | — |
| 10 | 35 | — |
| 11* | 40 | — |

*after NaOH cleaning

EXAMPLE 9

A cross-linked ultrafiltration membrane prepared in accordance with Example 4 was used to filter oil from a spent alkaline degreasing bath of pH 14. The filtration was carried out in a stirring cell at a pressure of 4 bar and at room temperature. The filtration capacity at the beginning measured 30 l/h·m² and dropped upon reaching a concentration of 10 to 5 l/h·m². The membrane surface permitted oil residues to be completely rinsed off. Subsequently, the membrane was stored 35 days in the spent alkaline degreasing bath and the filtration operation repeated. The filtration capacity dropped to only 29 l/h·m².

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A process of making a cross-linked cellulose hydrate membrane comprising contacting a cellulose hydrate membrane with an aqueous alkaline solution of a water-soluble diepoxide.

2. The process of claim 1 wherein said diepoxide has a water solubility of $\geq 0.2M$.

3. The process of claim 1 wherein said solution has a diepoxide concentration of about 0.2 to about 2.0M.

4. The process of claim 1 wherein said solution has a diepoxide concentration of about 0.3 to about 1.0M.

5. The process of claim 1 wherein said diepoxide is 5-ethyl-1,3-diglycidyl-5-methylhydantoin.

6. The process of claim 1 conducted at a temperature of 0° to 50° C. wherein said solution has an alkaline concentration of 0.05 to 0.3 equivalents/l.

7. The process of claim 1 wherein said cellulose hydrate membrane is supported.

8. The process of claim 1 conducted by heating at a temperature of from 80° to 150° C. from 0.5 to minutes.

9. The process of claim 1 conducted in the presence of an inorganic neutral salt.

10. The process of claim 9 wherein said inorganic neutral salt is sodium sulphate.

11. A membrane comprising the product of the process of claims 1, 5 or 10.

12. The membrane of claim 11 having a degree of cross-linking of 0.05 to 0.5.

13. The membrane of claim 11 having a degree of cross-linking of 0.06 to 0.4.

14. The membrane of claim 12 having a degree of cross-linking of 0.12 to 0.25.

\* \* \* \* \*

UNITED STATES PATENT AND TRADEMARK OFFICE
CERTIFICATE OF CORRECTION

PATENT NO. : 5,739,316

DATED : April 14, 1998

INVENTOR(S) : Beer et al.

It is certified that error appears in the above-indentified patent and that said Letters Patent is hereby corrected as shown below:

Col. 2, line 30: delete "a" before -- non-cross-linked --

Col. 4, line 53: change "ultrafitaioh" to read -- ultrafiltration --

Col. 8, line 5-6: put "a", "b", and "d" in bold typeface

Col. 9, line 11: insert -- 10 -- before "minutes"

Signed and Sealed this

Twentieth Day of July, 1999

Attest:

Q. TODD DICKINSON

Attesting Officer

Acting Commissioner of Patents and Trademarks